(12) United States Patent
Rushdy et al.

(10) Patent No.: US 6,319,284 B1
(45) Date of Patent: Nov. 20, 2001

(54) TOE IMPLANT

(75) Inventors: Jamal Rushdy, Carlsbad; Bruce R. Lawrence, Oceanside, both of CA (US)

(73) Assignee: Futura Biomedical LLC, Vista, CA (US)

( * ) Notice: Subject to any disclaimer, the term of this patent is extended or adjusted under 35 U.S.C. 154(b) by 0 days.

(21) Appl. No.: 09/584,279

(22) Filed: May 31, 2000

(51) Int. Cl.⁷ .......................................................... A61F 2/42
(52) U.S. Cl. ............................... 623/21.19; 623/21.11; 623/18.11
(58) Field of Search ................................. 623/21.19, 21, 623/18.11, 21.11; D24/33

(56) References Cited

U.S. PATENT DOCUMENTS

| D. 277,509 | 2/1985 | Lawrence et al. . |
| D. 284,099 | 6/1986 | Laporta et al. . |
| D. 291,731 | * 9/1987 | Aikins .................................... D24/33 |
| 3,654,186 | * 4/1972 | Dee ................................................. 3/1 |
| 4,198,713 | 4/1980 | Swanson . |
| 4,871,367 | * 10/1989 | Christensen et al. ................... 623/21 |

OTHER PUBLICATIONS

Futura Biomedical, "The Lawrence Great Toe Metatarsophalangeal Joint Implant", 1999, Futura Biomedical, pp.1–4.*

* cited by examiner

Primary Examiner—Corrine McDermott
Assistant Examiner—Thomas Barrett
(74) Attorney, Agent, or Firm—Steven G. Roeder

(57) ABSTRACT

A toe implant (10) for a first metatarsal phalangeal joint (22) between a metatarsal (24) and a proximal phalanx (26) of a great toe (12) includes a proximal stem (16), a distal stem (18) and a hinge (20) and a strength rib (92). Importantly, the toe implant (10) is designed to accommodate an axis of motion in a unique location (82) and the distal stem (18) is naturally positioned lower than the proximal stem (16). Further, the toe implant (10) provides a relatively good available range of motion. With this design, the toe implant (10) maintains the proximal phalanx (26) in the correct anatomic position relative to the metatarsal (24) during bending and flexing. Additionally, the toe implant (10) allows the toe (12) to move in a fashion that simulates the natural motion of the first metatarsal phalangeal joint (22). As a result thereof, the toe implant (10) that does not significantly increase the stress at the joint (22) or alter the normal flexing of the toe (12).

33 Claims, 4 Drawing Sheets

TOE IMPLANT

FIELD OF THE INVENTION

The present invention is directed to a toe implant. More specifically, the present invention is directed to a double-stemmed toe implant that is used to supplement a first metatarsal phalangeal joint arthroplasty of the great toe.

BACKGROUND

It is well know that some people have problems with one or more joints in their feet. Examples of problems include a rigid or limited range of motion in one or more joints, painful rheumatoid arthritis in one or more joints, deformed bones associated with arthritis, and/or unstable or painful joints from previous surgeries.

Several procedures have been developed to treat these conditions. For example, intra-articular soft tissue procedures, arthrodesis, and Keller arthroplasty have been developed for the first metatarsal phalangeal joint. An intra-articular soft tissue procedure involves reconstructing the joint utilizing soft tissue structures within and around the joint. An arthrodesis procedure involves the fusion of the bones of the joint. A Keller arthroplasty procedure involves the reconstruction of the joint after removal of a portion of the bone from the joint.

Unfortunately, none of these procedures or treatments is completely satisfactory. For example, intra-articular soft tissue procedures are successful for only a limited range of patients. Arthrodesis is effective in eliminating pain but at the expense of joint immobility, load transfer complications, and limited shoe wear options. Keller arthroplasty frequently relieves pain but sometimes results in an unstable toe and loss of toe purchase due to muscle weakness and imbalance.

An alternate solution to the problem includes the use of a double stemmed implant to combat the destructive processes in the joints of the foot. One type of implant 10P is illustrated in FIGS. 1A and 1B. In particular, FIG. 1A illustrates the implant 10P in a relaxed condition, while FIG. 1B illustrates the implant 10P (partly in phantom) positioned in a first metatarsal phalangeal joint 12P of a great toe 14P. In FIG. 1B, the toe 14P is flexed. Additionally, the sesamoid apparatus 15P is illustrated in FIG. 1B.

The implant 10P includes a proximal stem 16P, a distal stem 18P, a hinge 20P and a pair of metal grommets 22P. The proximal stem 16P is inserted into the metatarsal 24P while the distal stem 18P is inserted into the proximal phalanx 26P. The implant 10P is designed to flex at the center of the hinge 20P. The grommets 22P are positioned on opposite sides to the hinge 20P. The implant 10P is sold by Wright Medical Technology, Inc. located in Arlington, Tenn., under the trademark "SWANSON®".

Unfortunately, the results obtained with the implant 10P illustrated in FIGS. 1A and 1B are not entirely satisfactory. More specifically, the implant 10P must deform to accommodate the anatomy of the first metatarsal phalangeal joint 12P. As a result thereof, the implant 10P limits the range of motion of the joint 12P, increases the stress at the joint 12P and/or alters the normal flexing of the toe 14P.

Further, the deformation of the implant 10P can cause binding in the joint 12P. Moreover, referring to FIG. 1B, the grommets 22P can contact during flexing of the toe 14P.

Furthermore, the cuts to metatarsal 24P and/or the proximal phalanx 26P required to make space for the implant 10P can interfere with the sesamoid apparatus 15P or the flexor hallucis brevis attachment (not illustrated in FIG. 1B). This can significantly influence how the toe 14P functions with the implant 10P.

In light of the above, it is an object of the present invention to provide a toe implant for the first metatarsal phalangeal joint for the great toe that provides increased available range of motion. Another object of the present invention is to provide a toe implant that allows the toe to move in a fashion that better simulates the natural motion of the first metatarsal phalangeal joint. Still another object of the present invention is to provide a toe implant that does not significantly increase the stress at the joint or alter the normal flexing of the toe. Yet another object of the present invention is to provide a toe implant that does not interfere with the sesamoid apparatus or the flexor hallucis brevis attachment. Another object is to provide a toe implant that provides relatively good joint mobility, relatively good load transfer, relatively good toe stability, and relatively good toe purchase. Still another object is to provide a toe implant that is relatively easy to insert into the first metatarsal phalangeal joint.

SUMMARY

The present invention is directed to a toe implant that satisfies these objectives. The toe implant is particularly useful as a first metatarsal phalangeal joint between the proximal phalanx and the metatarsal of a great toe. The toe implant includes an implant body having a proximal stem, a distal stem, and a hinge. The hinge is positioned between and connects the proximal stem to the distal stem. The hinge includes a hinge center, a proximal hinge buttress and a distal hinge buttress. The proximal stem extends away from the proximal hinge buttress and the distal stem extends away from the distal hinge buttress.

Uniquely, the implant body is designed to accommodate an axis of motion at an area that is not at the hinge center when toe implant is inserted in the toe. More specifically, the implant body is designed to accommodate an axis of motion near the proximal hinge buttress. With this design, the toe implant maintains the proximal phalanx in the correct anatomic position relative to the metatarsal during bending and flexing and allows the toe to move in a fashion that simulates the natural motion of the first metatarsal phalangeal joint.

The proximal stem includes a proximal axis and the distal stem includes a distal axis. Importantly, the distal axis is offset relative to the proximal axis. More specifically, the distal axis is positioned below the proximal axis. Further, the proximal hinge buttress is axially offset from the distal hinge buttress. With this configuration, the distal stem is better able to match and provide a better anatomic fit in the medullary canal of the proximal phalanx. Additionally, the toe implant is better able to match and maintain the natural position of the proximal phalanx relative to the metatarsal during movement of the toe. As a result thereof, there is less stress created by the toe implant and the toe implant does not alter the normal flexing of the toe.

Additionally, the proximal hinge buttress is preferably at an angle of between approximately forty-five degrees and seventy-five degrees relative to the proximal axis. Further the distal hinge buttress is preferably at an angle of between approximately sixty-five degrees and eighty-five degrees relative to the distal axis. With this design, the cuts required to the metatarsal and the proximal phalanx to make space for the toe implant do not interfere with the sesamoid apparatus or the flexor hallucis brevis attachment. This feature also allows the toe to move in a fashion that simulates the natural motion of the first metatarsal phalangeal joint.

The hinge includes an upper cutout and a lower cutout that allow the implant body to flex through a range of motion through plantar flexure and dorsal flexure of between at least approximately seventy-five degrees and ninety-five degrees. This feature allows the toe implant to provide a relatively good available range of motion in the first metatarsal phalangeal joint, without significantly increasing the stress at the joint or altering the normal flexing of the toe.

Additionally, the hinge can include a strength rib that is positioned in the lower cut-out. The thickness of the strength rib can be varied along the length of the strength rib to influence the bending characteristics of the toe implant. For example, the strength rib can be thicker near the hinge center of the hinge than near the edges of the hinge. With this design, the strength rib adds material to the center of the hinge to strengthen the central axis of the implant, while allowing for medial-lateral bending at the edges. This feature reduces internal implant stresses incurred from medial-lateral forces.

In summary, the toe implant has a number of unique features that allow for good joint mobility, relatively good load transfer, pain relief, relatively good toe stability, relatively good toe purchase, and consistent and reliable results.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION

Figure 1A:
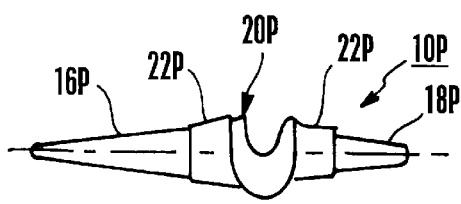
FIG. 1A is a side plan view of a prior art toe implant.
Figure 1B:
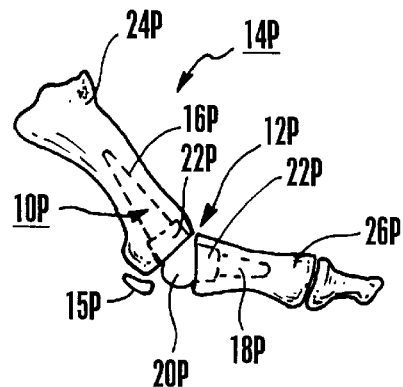
FIG. 1B is a side plan view of the prior art toe implant of FIG. 1A positioned in a flexed great toe.
Figure 2:
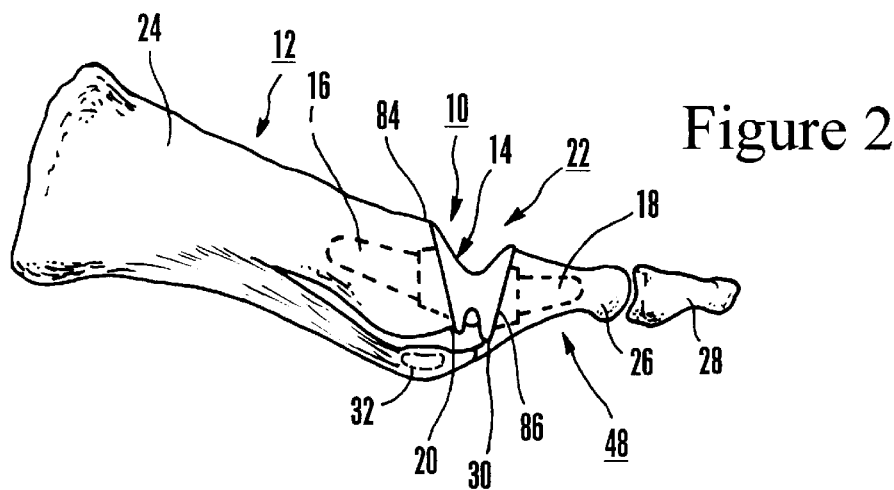
FIG. 2 is a side plan view of a toe implant having features of the present invention positioned in a toe.
Figure 3:
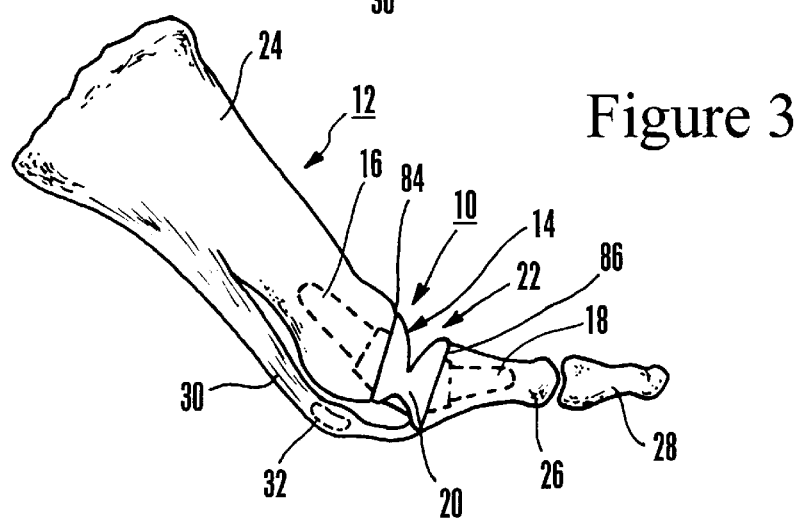
FIG. 3 is a side plan view of the toe implant and toe of FIG. 2, with the toe and implant flexed.
Figure 4:
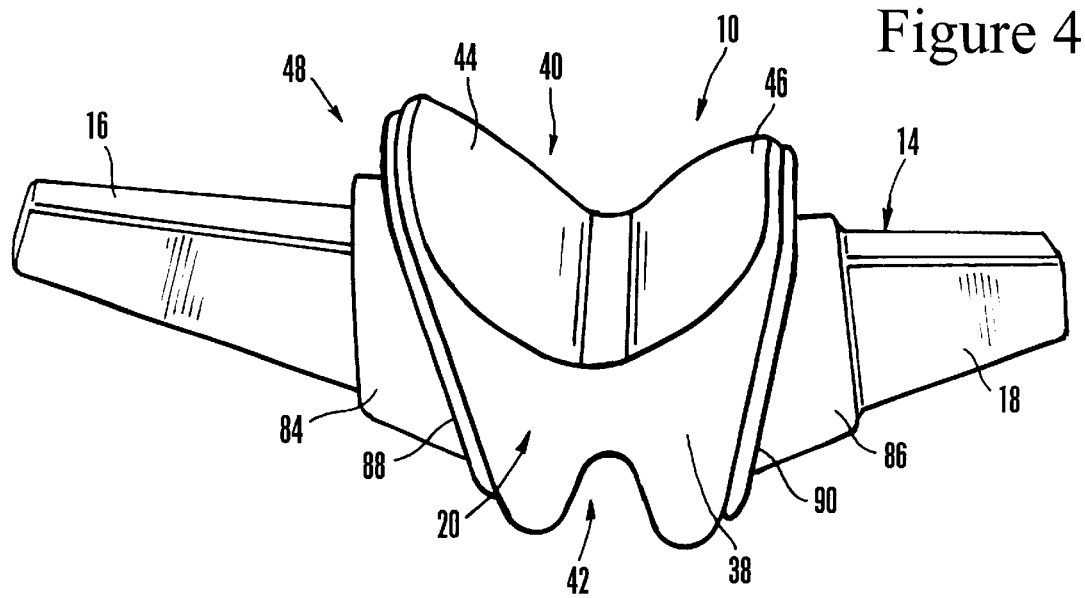
FIG. 4 is an enlarged perspective view of the toe implant of FIG. 2.

Referring initially to FIGS. 2–5, a toe implant 10 for a toe 12 having features of the present invention includes an implant body 14 having a proximal stem 16, a distal stem 18 and a hinge 20. The toe implant 10 is particularly useful as a replacement joint 22 in the great toe 12. More specifically, the toe implant 10 is particularly useful in the first metatarsal phalangeal joint 22 between the metatarsal 24 and the proximal phalanx 26. The distal phalanx 28, the flexor hallucis brevis attachment 30 and the sesamoid apparatus 32 (illustrated in phantom) of the toe 12 are also illustrated in FIGS. 2 and 3.

As provided in detail below and illustrated in FIGS. 2 and 3, the toe implant 10 is uniquely designed to maintain the proximal phalanx 26 in the correct anatomic position relative to the metatarsal 24 during bending and flexing. Stated another way the toe implant 10 is designed to account for the unique geometry and motion of the first metatarsal phalangeal joint 22. Thus, the toe implant 10 allows the metatarsal 24 to move in a fashion that simulates the natural motion of the first metatarsal phalangeal joint 22. Further, the toe implant 10 provides a relatively good available range of motion in the first metatarsal phalangeal joint 22.

As a result thereof, the toe implant 10 does not significantly increase the stress at the joint 22 or alter the normal flexing of the metatarsal 24. Further, the toe implant 10 provides good joint mobility, relatively good load transfer, relatively good toe stability, and relatively good toe purchase.

The proximal stem 16 inserts into a medullary canal in the metatarsal 24. Referring to FIGS. 4–7E, in the embodiment illustrated in the Figures, the proximal stem 16 has a cross-section that is generally rectangular shaped. Further, the cross-sectional shape of the proximal stem 16 tapers as the distance from the hinge 20 increases. Additionally, the corners of the proximal stem 16 are slightly rounded. Alternately, other shapes of the proximal stem 16 are possible.

Somewhat similarly, the distal stem 18 inserts into a medullary canal in the proximal phalanx 26. Referring to FIGS. 4–7E, in the embodiment illustrated in the Figures, the distal stem 18 has a cross-section that is generally trapezoidal shaped. The cross-sectional shape of the distal stem 18 tapers as the distance from the hinge 20 increases. Additionally, the corners of the distal stem 18 are slightly rounded. Alternately, other shapes of the distal stem 18 are possible.

It should be noted from the Figures that the proximal stem 16 is longer than the distal stem 18. Typically for the design provided herein, the proximal stem 16 has a proximal length 31A that is between approximately twenty-five percent and forty-five percent longer and more preferably approximately thirty-five percent longer than a distal length 31B the distal stem 18.

The hinge 20 connects the proximal stem 16 to the distal stem 18. The hinge 22 includes a proximal hinge buttress 34, a distal hinge buttress 36, a hinge center section 38, an upper cut-out 40 and a lower cutout 42. Preferably, the proximal stem 16 extends away from a center of the proximal hinge buttress 34 while the distal stem 18 extends away from a center of the distal hinge buttress 36.

The proximal hinge buttress 36 is somewhat rectangular shaped and matches the geometry of the resected metatarsal base. Alternately, the distal hinge buttress is somewhat trapezoidal shaped and matches the geometry of resected proximal phalanx base.

The hinge center section 38 connects the proximal hinge buttress 34 and the distal hinge buttress 36. The hinge center section 38 includes a hinge center 43 (illustrated as a dot in FIGS. 5, 6, and 7E). Further, the hinge center section 38 is defined by and separates the upper cutout 40 from the lower cutout 42. Each of the cutouts 40, 42 is generally V shaped. However, the upper cutout 40 is much larger and deeper than the lower cutout 42. Each of the cutouts 40, 42 is positioned between the proximal hinge buttress 34, the hinge center section 38 and the distal hinge buttress 36. Each of the cutouts 40, 42 includes a proximal side 44 and a distal side 46.

Figure 5:
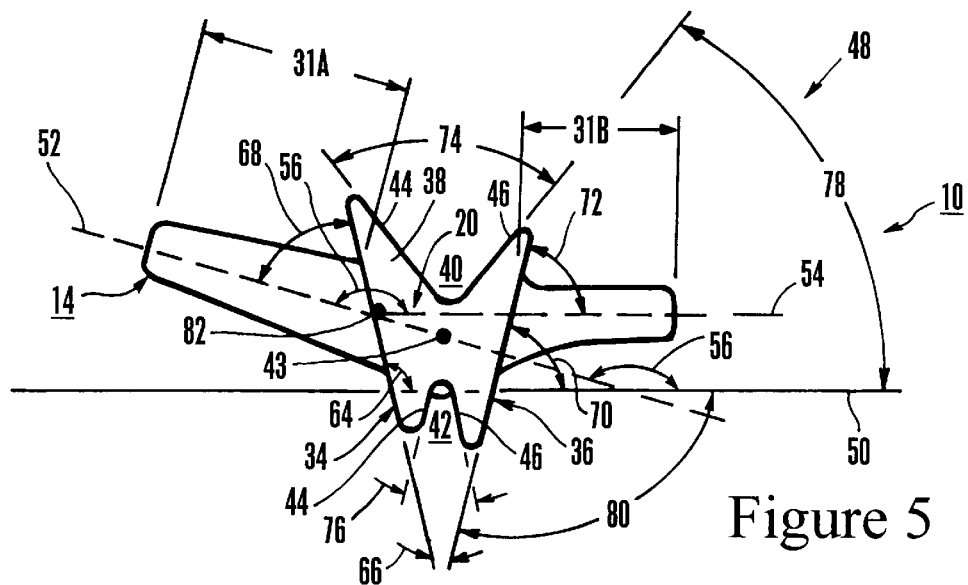
FIG. 5 is a side plan view of the toe implant of FIG. 2 without grommets.

FIGS. 2, 4, 5 and 7E illustrate the toe implant 10 in a relaxed, inserted position 48. In the relaxed inserted position 48, the toe implant 10 is not flexed and the toe implant 10 is oriented as if it is inserted in a non-flexed toe. In fact, FIG. 2 illustrates the toe implant 10 in the relaxed, inserted position 48 within a non-flexed toe 12. FIG. 5 includes a horizontal reference line 50 to illustrate orientation of the toe implant 10 in the relaxed, inserted position 48.

Referring to FIG. 5, in the relaxed, inserted position 48, a distal axis 54 of the distal stem 18 is substantially parallel with the horizontal reference line 50. This feature allows the distal stem 18 of the toe implant 10 to correspond with the natural orientation of the proximal phalanx 26. Further, in the relaxed, inserted position 48, a proximal axis 52 of the proximal stem 16 is angled relative to the horizontal reference line 50 and the distal axis 54. More specifically, in the relaxed, inserted position 48, the proximal axis 52 is at an angle 56 of between approximately one hundred and fifty degrees and one hundred and eighty degrees and more preferably approximately one hundred and sixty-five degrees relative to the distal axis 54 and the horizontal reference line 50. This feature allows the proximal stem 16 of the toe implant 10 to correspond with the natural declination angle of the metatarsal 24.

Figure 6:
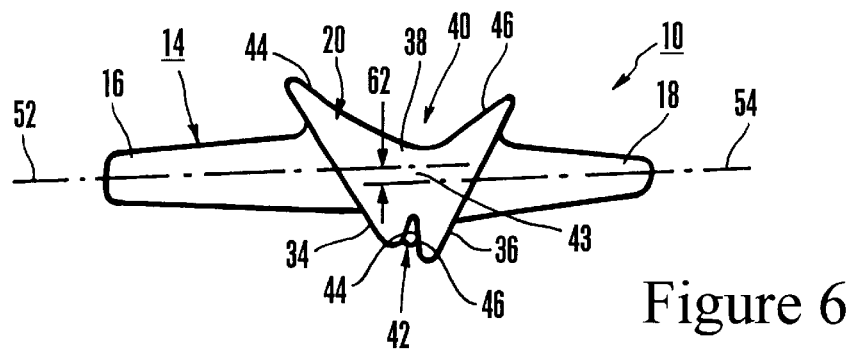
FIG. 6 is a side plan view of the toe implant of FIG. 2 without grommets, with the toe implant flexed.

Another unique design feature of toe implant 10 is that the distal axis 54 is offset 62 from the proximal axis 54. This feature can probably best be understood with reference to FIG. 6. FIG. 6 is a side view, with the toe implant 10 bent so that the proximal axis 52 is substantially parallel with the distal axis 54. In this position, the distal axis 54 is between approximately one millimeter and two millimeters lower than the proximal axis 52. Stated another way, the distal stem 18 is plantar offset 62 from the proximal stem 16. With this configuration, the distal stem 18 is better able to match and provide a better anatomic fit in the medullary canal of the proximal phalanx 26. Further, the toe implant 10 matches the position of the proximal phalanx 26 relative to the metatarsal 24 and maintains the proximal phalanx 26 lower than the metatarsal 24. Because, the distal stem 18 is offset and lower than the proximal stem 16, there is less stress created by the toe implant 10 and the toe implant 10 functions better.

Figure 7A:
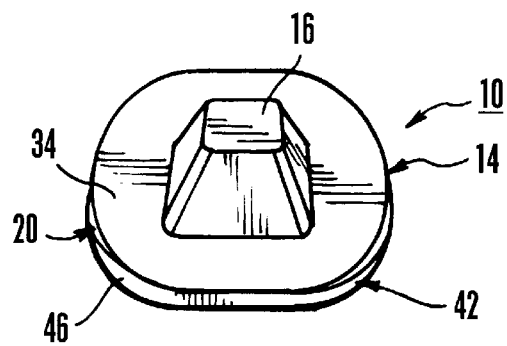
FIG. 7A is a proximal end view of the toe implant of FIG. 2 without grommets.
Figure 7B:
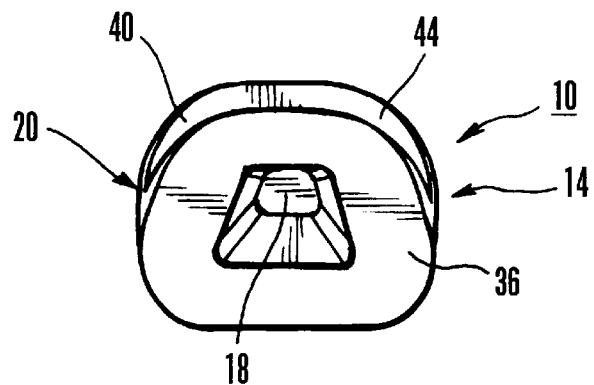
FIG. 7B is a distal end view of the toe implant of FIG. 2 without grommets.
Figure 7C:
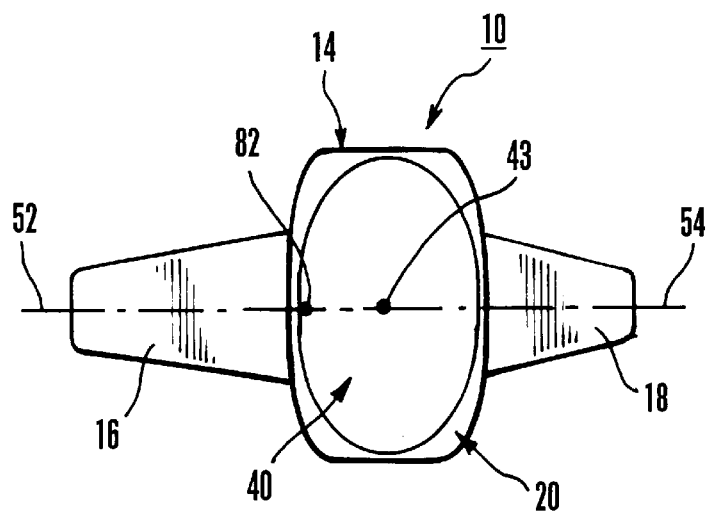
FIG. 7C is a top plan view of the toe implant of FIG. 2 without grommets.
Figure 7D:
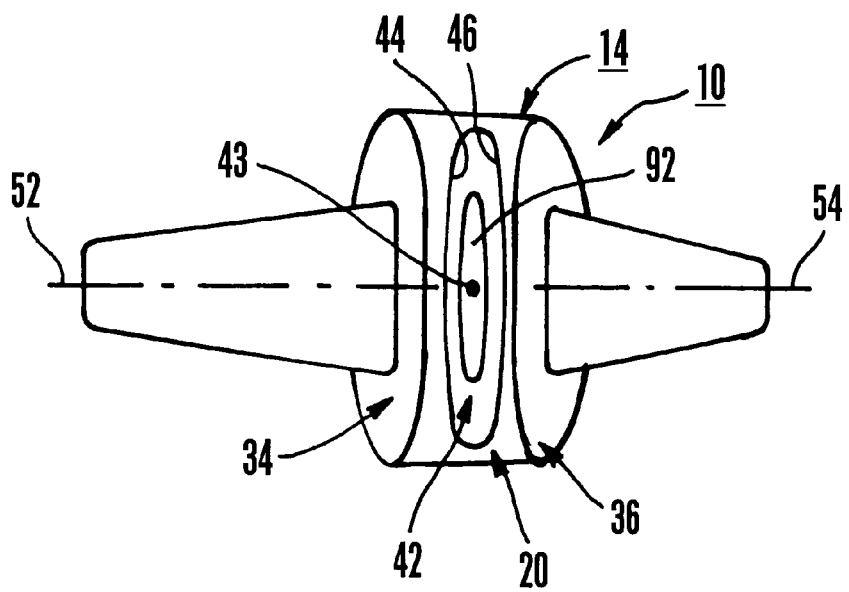
FIG. 7D is a bottom plan view of the toe implant of FIG. 2 without grommets.
Figure 7E:
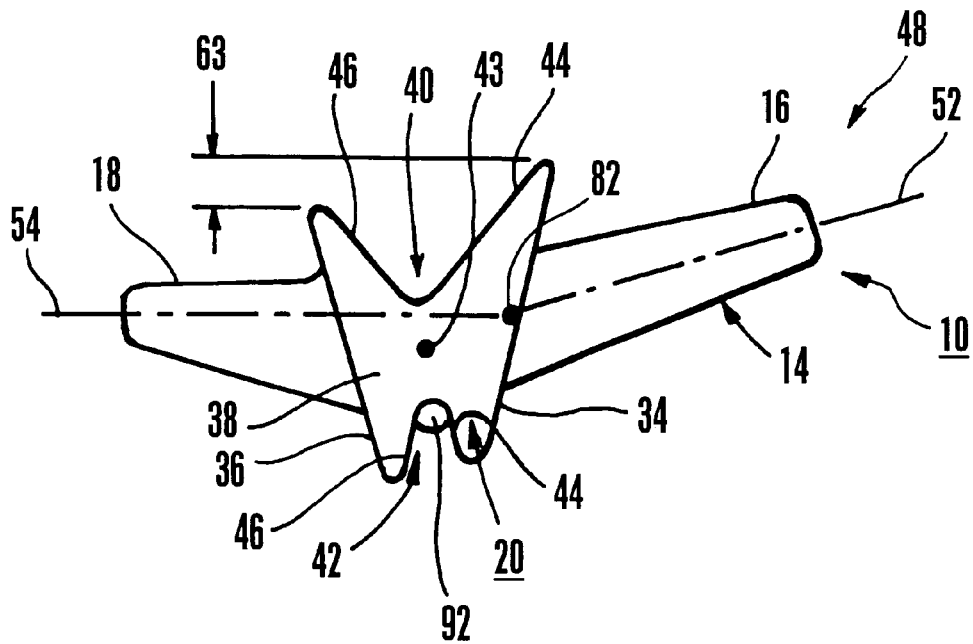
FIG. 7E is a back side, plan view of the toe implant of FIG. 2 without grommets.

Additionally, referring to FIG. 7E, the proximal hinge buttress 34 is axial offset 63 from the distal hinge buttress 36. In particular, in the relaxed, inserted position 48, the proximal hinge buttress 34 is offset 63 from and positioned between approximately two millimeters and four millimeters higher than the distal hinge buttress 36. In this embodiment, the proximal stem 16 extends away from the center of the proximal hinge buttress 34 and the distal stem 18 extends away from the center of the distal hinge buttress 36. Thus, the distal stem 18 is offset from and lower than the proximal stem 16.

In the relaxed, inserted position 48, the proximal hinge buttress 34 is at an angle 64 of between approximately ninety-five degrees and one hundred and fifteen degrees and more preferably approximately one hundred and five degrees relative to the horizontal reference line 50. Further, the proximal hinge buttress 34 is at an angle 66 of between approximately twenty degrees and forty degrees and more preferably approximately thirty degrees relative to the distal hinge buttress 36. Additionally, the proximal hinge buttress 34 is at an angle 68 of between approximately forty-five degrees and seventy-five degrees and more preferably approximately sixty degrees relative to the proximal axis 52. Because of angulation of the proximal hinge buttresses 34, the toe implant 10 can be inserted without making cuts that interfere with the sesamoid apparatus 32. This allows for more natural flexing and motion of the toe 12.

The distal hinge buttress 36 is at an angle 70 of between approximately sixty-five degrees and eighty-five degrees and more preferably approximately seventy-five degrees relative to the horizontal position reference line 50. Further, the distal hinge buttress 36 is at an angle 72 of between approximately sixty-five degrees and eighty-five degrees and more preferably approximately seventy-five degrees relative to the distal axis 54. Because of angulation of the distal hinge buttresses 34, the toe implant 10 can be inserted without making cuts that interfere with the flexor hallucis brevis attachment 30. As a result thereof, the toe 12 with the toe implant 10 is able to have good toe purchase.

The upper cutout 40 and the lower cutout 42 are located and sized to allow for between approximately seventy-five degrees and one hundred and five degrees of available range of motion and more preferably at least approximately 95 degrees of available range of motion. Referring to FIG. 5, in the relaxed, inserted position 48, the proximal side 44 and the distal side 48 of the upper cutout 40 cooperate to form an angle 74 of between approximately seventy degrees and ninety degrees and more preferably approximately eighty degrees. Alternately, in the relaxed, inserted position 48, the proximal side 44 and the distal side 46 of the lower cutout 42 cooperate to form an angle 76 of between approximately fifteen degrees and thirty-five degrees and more preferably approximately twenty-six degrees.

In the relaxed, inserted position 48, the distal side 46 of the upper cutout 40 is at an angle 78 of between approximately forty degrees and sixty degrees relative to the horizontal reference line 50. Alternately, in the relaxed, inserted position 48, the distal side 46 of the lower cutout 42 is at an angle 80 of between approximately ninety-five degrees and one hundred and fifteen degrees relative to the horizontal reference line 50.

Additionally, the hinge 20 can include a strength rib 92 that extends along the hinge center section 38. In the embodiment illustrated in the Figures, the strength rib 92 is positioned in the lower cut-out 42. Further, in the embodiment illustrated in the Figures, the strength rib 92 has an arc shaped cross-section and the strength rib 92 is integrally formed with the rest of the implant body 14.

Preferably, the strength rib 92 is thicker near the hinge center 43 than near the edges of the hinge 20. More specifically, the thickness of the strength rib 92 near the hinge center 43 is between approximately twenty percent to sixty percent and more preferably between approximately thirty percent and forty percent greater than near the edges of the hinge 20. With this design, the strength rib 92 adds material to the center of the hinge 20 to strengthen the central axis of the toe implant 10, but allows for medial-lateral bending at the edges. This feature reduces internal implant 10 stresses incurred from medial-lateral forces generated during use of the implant 10.

With the design provided herein, the toe implant 10 accommodates an axis of motion at a location 82 that is not at the hinge center 43. More specifically, the toe implant 10 accommodates an axis of motion at an area 82 (represented by a dot in FIGS. 5, 7C and 7E) that is near the proximal hinge buttress 34. Even more specifically, the area 82 is located intermediate the proximal hinge buttress 34 and the hinge center 43. With this design, the toe implant 10 is better able to simulate the natural bending of the first metatarsal phalangeal joint 22.

The implant body 14 can be made of a number of materials including medical grade silicone elastomers. Preferably, the implant body 14 is made as a continuous, uniform, single component.

Preferably, the toe implant 10 includes a proximal grommet 84 and a distal grommet 86. The grommets 84, 86 protect the implant 10 from osseous engulfment and provide added wear protection for the implant body 14. Preferably, the proximal grommet 84 includes a proximal contact surface 88 that matches the geometry of the resected metatarsal base. Similarly, the distal grommet 86 preferably includes a distal contact surface 90 that matches the geometry of resected proximal phalanx base.

Each grommet 84, 86 can be made of titanium, or some other suitable material. The grommets 84, 86 are preferably press-fit into the resected bone ends without protruding into the soft tissue. As illustrated in FIG. 3, the upper cutout 40 is designed to inhibit grommet 84-on-grommet 86 contact and wear.

Importantly, the toe implant 12 maintains the proximal phalanx 26 in the correct anatomic position relative to the metatarsal 24 during bending and flexing. Further, the toe implant 10 allows the toe 12 to move in a fashion that simulates the natural motion of the first metatarsal phalangeal joint 22. As a result thereof, the toe implant 10 that does not significantly increase the stress at the joint 22 or alter the normal flexing of the toe 12. Further, the toe implant 10 provides good joint mobility, relatively good load transfer, pain relief, relatively good toe stability, and relatively good toe purchase.

While the particular toe implant 10 as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A toe implant for a toe, the toe implant comprising:
an implant body including a proximal stem, a distal stem, and a hinge, the hinge being positioned between and connecting the proximal stem to the distal stem, the distal stem including a bottom surface, the proximal stem including a bottom surface, wherein the bottom surface of the distal stem near the hinge is positioned below the bottom surface of the proximal stem near the hinge when the insert body is in a relaxed inserted position.

2. The toe implant of claim 1 wherein the distal stem includes a top surface and a distal axis, and the proximal stem includes a top surface and a proximal axis, and wherein the top surface of the distal stem near the hinge is positioned below the top surface of the proximal stem near the hinge, and the distal axis of the distal stem is positioned below the proximal axis of the proximal stem.

3. The toe implant of claim 1 wherein the hinge includes a proximal hinge buttress and a distal hinge buttress, the proximal stem extends away from the proximal hinge buttress and the distal stem extends away from the distal hinge buttress and wherein when the proximal stem and the proximal hinge buttress are pivoted upward relative to the rest of the implant body, the implant body has an axis of motion at a location that is (i) between the proximal hinge buttress and a hinge center of the hinge and (ii) above the hinge center.

4. The toe implant of claim 3 wherein the proximal hinge buttress is positioned higher than the distal hinge buttress when the implant body is in the relaxed inserted position.

5. The toe implant of claim 1 wherein the hinge includes a proximal hinge buttress and a distal hinge buttress, the proximal stem extends away from the proximal hinge buttress and the distal stem extends away from the distal hinge buttress wherein the proximal hinge buttress is at an angle of between approximately ninety-five degrees and one-hundred and fifteen degrees relative to a horizontal reference line when the toe implant is in the relaxed inserted position.

6. The toe implant of claim 5 wherein the distal hinge buttress is at an angle of between approximately sixty-five degrees and eighty-five degrees relative to a horizontal reference line when the toe implant is in a relaxed inserted position.

7. The toe implant of claim 1 including a strength rib that extends along a hinge center section of the hinge, the strength rib having a thickness transversely across the rib that varies along the length of the strength rib.

8. The toe implant of claim 7 wherein the strength rib is between approximately twenty to sixty percent thicker transversely across the rib near a hinge center than near the edges of the rib.

9. The toe implant of claim 1 wherein the distal stem has a trapezoidal shaped cross-section.

10. A toe implant for a toe, the toe implant comprising:
an implant body including a proximal stem, a distal stem, and a hinge, the hinge being positioned between and connecting the proximal stem to the distal stem, the hinge including a proximal hinge buttress, a distal hinge buttress and a hinge center, the proximal stem extends away from the proximal hinge buttress and the distal stem extends away from the distal hinge buttress; wherein the proximal hinge buttress is positioned higher than the distal hinge buttress when the implant body is in a relaxed inserted position; and wherein when the proximal stem and the proximal hinge buttress are pivoted upward relative to the rest of the implant body, the implant body has an axis of motion at a location that is (i) between the proximal hinge buttress and the hinge center and (ii) above the hinge center.

11. The toe implant of claim 10 wherein the distal stem includes a top surface, a distal axis, and a bottom surface, and the proximal stem includes a top surface, a proximal axis and a bottom surface, and wherein the top surface of the distal stem adjacent the distal hinge buttress is positioned below the top surface of the proximal stem adjacent the proximal hinge buttress, the distal axis of the distal stem is positioned below the proximal axis of the proximal stem, and the bottom surface of the distal stem adjacent the distal hinge buttress is positioned below the bottom surface of the proximal stem adjacent the proximal hinge buttress.

12. The toe implant of claim 10 wherein the proximal stem includes a proximal axis and the distal stem includes a distal axis, the distal axis is offset relative to the proximal axis, and the distal axis is positioned lower than the proximal axis.

13. The toe implant of claim 10 wherein the proximal hinge buttress is at an angle of between approximately ninety-five degrees and one-hundred and fifteen degrees relative to a horizontal reference line when the toe implant is in a relaxed inserted position.

14. The toe implant of claim 13 wherein the distal hinge buttress is at an angle of between approximately sixty-five degrees and eighty-five degrees relative to a horizontal reference line when the toe implant is in the relaxed inserted position.

15. The toe implant of claim 10 including a strength rib that extends along a hinge center section of the hinge, the strength rib having a thickness transversely across the rib that varies along the length of the strength rib.

16. The toe implant of claim 1 wherein the strength rib is between approximately twenty to sixty percent thicker transversely across the rib near a hinge center than near the edges of the hinge.

17. The toe implant of claim 10 wherein the distal stem has a trapezoidal shaped cross-section.

18. A toe implant for a toe, the toe implant comprising: an implant body including a proximal stem, a distal stem, and a hinge, the hinge being positioned between and connecting the proximal stem to the distal stem, the hinge including a proximal hinge buttress and a distal hinge buttress, the proximal stem extends away from the proximal hinge buttress and the distal stem extends away from the distal hinge buttress and wherein the proximal hinge buttress is at an angle of between approximately ninety-five degrees and one-hundred and fifteen degrees relative to a horizontal reference line when the toe implant is in a relaxed inserted position.

19. The toe implant of claim 18 wherein the distal stem includes a top surface, a distal axis, and a bottom surface, and the proximal stem includes a top surface, a proximal axis and a bottom surface, and wherein the top surface of the distal stem adjacent the distal hinge buttress is positioned below the top surface of the proximal stem adjacent the proximal hinge buttress, the distal axis of the distal stem is positioned below the proximal axis of the proximal stem, and the bottom surface of the distal stem adjacent the distal hinge buttress is positioned below the bottom surface of the proximal stem adjacent the proximal hinge buttress.

20. The toe implant of claim 19 wherein the distal hinge buttress is positioned lower than the proximal hinge buttress when the implant body is in the relaxed inserted position.

21. The toe implant of claim 20 wherein when the proximal stem and the proximal hinge buttress are pivoted upward relative to the rest of the implant body, the implant body has an axis of motion at a location that is (i) between the proximal hinge buttress and a hinge center of the hinge and (ii) above the hinge center.

22. The toe implant of claim 18 wherein the distal hinge buttress is at an angle of between approximately sixty-five degrees and eighty-five degrees relative to a horizontal reference line when the toe implant is in the relaxed inserted position.

23. The toe implant of claim 18 including a strength rib that extends along a hinge center section of the hinge, the strength rib having a thickness transversely across the rib that varies along the length of the strength rib.

24. The toe implant of claim 23 wherein the strength rib is between approximately twenty to sixty percent thicker transversely across the rib near a hinge center than near the edges of the rib.

25. The toe implant of claim 18 wherein the distal stem has a trapezoidal shaped cross-section.

26. A toe implant for a toe, the toe implant comprising: an implant body including a proximal stem, a distal stem, and a hinge, the hinge being positioned between and connecting the proximal stem to the distal stem, the hinge includes a proximal hinge buttress, a distal hinge buttress and a hinge center, the proximal stem extends away from the proximal hinge buttress and the distal stem extends away from the distal hinge buttress; the distal stem includes a top surface, a distal axis, and a bottom surface, the proximal stem includes a top surface, a proximal axis and a bottom surface; wherein the top surface of the distal stem adjacent the distal hinge buttress is positioned below the top surface of the proximal stem adjacent the proximal hinge buttress, the distal axis of the distal stem is positioned below the proximal axis of the proximal stem, and the bottom surface of the distal stem adjacent the distal hinge buttress is positioned below the bottom surface of the proximal stem adjacent the proximal hinge buttress; wherein when the proximal stem and the proximal hinge buttress are pivoted upward relative to the rest of the implant body, the implant body has an axis of motion at a location that is (i) between the proximal hinge buttress and the hinge center of the hinge and (ii) above the hinge center; wherein the distal hinge buttress is positioned lower than the proximal hinge buttress when the implant body is in a relaxed inserted position; wherein the proximal hinge buttress is at an angle of between approximately ninety-five degrees and one-hundred and fifteen degrees relative to a horizontal reference line and the distal hinge buttress is at an angle of between approximately sixty-five degrees and eighty-five degrees relative to the horizontal reference line when the toe implant is in the relaxed inserted position.

27. The toe implant of claim 26 including a strength rib that extends along a hinge center section of the hinge, the strength rib having a thickness transversely across the rib that varies along the length of the strength rib.

28. The toe implant of claim 27 wherein the strength rib is between approximately twenty to sixty percent thicker transversely across the rib near a hinge center than near the edges of the hinge.

29. The toe implant of claim 28 wherein the distal stem has a trapezoidal shaped cross-section.

30. The toe implant of claim 29 wherein the distal axis of the distal stem is substantially parallel with the horizontal reference line and the proximal axis of the proximal stem is at an angle between approximately one hundred and fifty degrees and one hundred and eighty degrees relative to the horizontal reference line.

31. An implant comprising an implant body including a proximal stem having a proximal axis, a distal stem, a hinge and a strength rib, the hinge being positioned between and connecting the proximal stem to the distal stem, the hinge including a hinge center section, wherein the strength rib extends along only a portion of the hinge center section of the hinge and does not extend completely across the hinge center section, wherein the rib has a length perpendicular to the proximal axis that is approximately equal to a width perpendicular to the proximal axis of the proximal stem near the hinge, wherein the length of the rib is substantially parallel to the width of the proximal stem.

32. The implant of claim 31 wherein the strength rib has a thickness transversely across the rib that varies along the length of the strength rib.

33. The toe implant of claim 32 wherein the strength rib is between approximately twenty to sixty percent thicker transversely across the rib near a hinge center than near the edges of the rib.

* * * * *